US00PP19463P2

(12) United States Plant Patent
Cevasco, Jr.

(10) Patent No.: US PP19,463 P2
(45) Date of Patent: Nov. 18, 2008

(54) LAVENDER PLANTS NAMED 'HANCEV'

(50) Latin Name: *Lavandula stoechas*
Varietal Denomination: HanCev

(76) Inventor: Robert Cevasco, Jr., P.O. Box 368, Pescadero, CA (US) 94080

( * ) Notice: Subject to any disclaimer, the term of this patent is extended or adjusted under 35 U.S.C. 154(b) by 0 days.

(21) Appl. No.: 11/986,837

(22) Filed: Nov. 27, 2007

(51) Int. Cl.
*A01H 5/00* (2006.01)

(52) U.S. Cl. ..... Plt./445
(58) Field of Classification Search ..... Plt./445
See application file for complete search history.

*Primary Examiner*—Annette H Para
(74) *Attorney, Agent, or Firm*—Penny J. Aguirre

(57) ABSTRACT

A new cultivar of *Lavendula stoechas,* 'HanCev', characterized by its dense, upright apical dominate plant habit, its vigorous growth habit, its floriferous and long blooming flower habit with its deep purple flowers and upright iridescent violet purple terminal flower bracts, its resistance to powdery mildew, and its tolerance to wind, rain and temperature extremes.

1 Drawing Sheet

Botanical classification: *Lavandula stoechas.*
Variety denomination: 'HanCev'.

BACKGROUND OF THE INVENTION

The present invention relates to a new and distinct cultivar of *Lavandula stoechas* and will be referred to hereafter by its cultivar name, 'HanCev'. 'HanCev' is a new variety of lavender suitable for landscape and container use.

The inventor discovered 'HanCev' in a block of containers at his nursery in Pescadero, Calif. is spring of 2006. 'HanCev' arose as a naturally occurring branch mutation of 'Otto Quasti' (syn. 'Otto Quast'), an unpatented cultivar.

The new cultivar was first asexually propagated by terminal stem cuttings in Pescadero, Calif. in May of 2007. Asexual propagation has determined that the characteristics of this cultivar are stable and are reproduced true to type in successive generations.

SUMMARY OF THE INVENTION

The following traits have been repeatedly observed and represent the characteristics of one year-old plants the new lavender as grown outdoors under nursery conditions in a one-gallon container. These attributes in combination distinguish 'HanCev' as a unique cultivar of lavender.

1. 'HanCev' exhibits an upright, apical dominant plant habit.
2. 'HanCev' exhibits a very vigorous growth habit, reducing crop production time in comparison to many other *Lavandula stoechas* cultivars grown by the inventor.
3. The sterile (terminal) bracts of 'HanCev' are long (3 to 5 cm in length), narrow (1 cm in width), slightly twisted, curved inward and held upright.
4. The 'HanCev' is floriferous with flower spikes that are dark purple with sterile terminal bracts that are a consistent shade of iridescent violet purple.
5. 'HanCev' is freely branched with a dense, shrub-like form.
6. 'HanCev' has shown more resistance to powdery mildew than is typical for cultivars of *Lavandula stoechas.*

7. 'HanCev' is tolerant to rain and wind and has survived temperatures ranging from 20° F. to over 100° F.

The new cultivar of lavender can be readily distinguished from its parent and other cultivars of lavender. 'HanCev' differs from its parent plant, 'Otto Quasti', in having a more upright apical dominant plant habit, foliage that is lighter green in color, a more vigorous growth habit, and sterile (terminal) bracts that are more curved, longer in length and held more upright. 'HanCev' can be compared to the cultivar 'Belpur' (U.S. Plant Pat. No. 16,861) as 'Belpur' has similar colored flower spikes and also exhibits a vigorous growth habit. In side-by-side comparisons, 'HanCev' differs from 'Belpur' in having a more upright apical dominant plant habit, sterile bracts that are longer, more curved, and held more upright, and foliage that is slightly darker green in color. 'HanCev' has also showed a more apical dominant plant habit and increased vigor in comparison to cultivars 'Madrid Purple' (not patented) and 'Barcelona Purple' (U.S. Plant Pat. No. 15,571) and unnamed plants of the species.

BRIEF DESCRIPTION OF THE DRAWING

The accompanying colored photograph in FIG. 1 illustrates the overall appearance and distinct characteristics of a six month-old plant of 'HanCev' as grown in a one-gallon outdoors in Pescadero, Calif. The photograph is as close as possible with the digital photography techniques utilized and the color values cited in the detailed botanical description more accurately describe the colors of the new lavender.

DETAILED BOTANICAL DESCRIPTION

Figure 1:
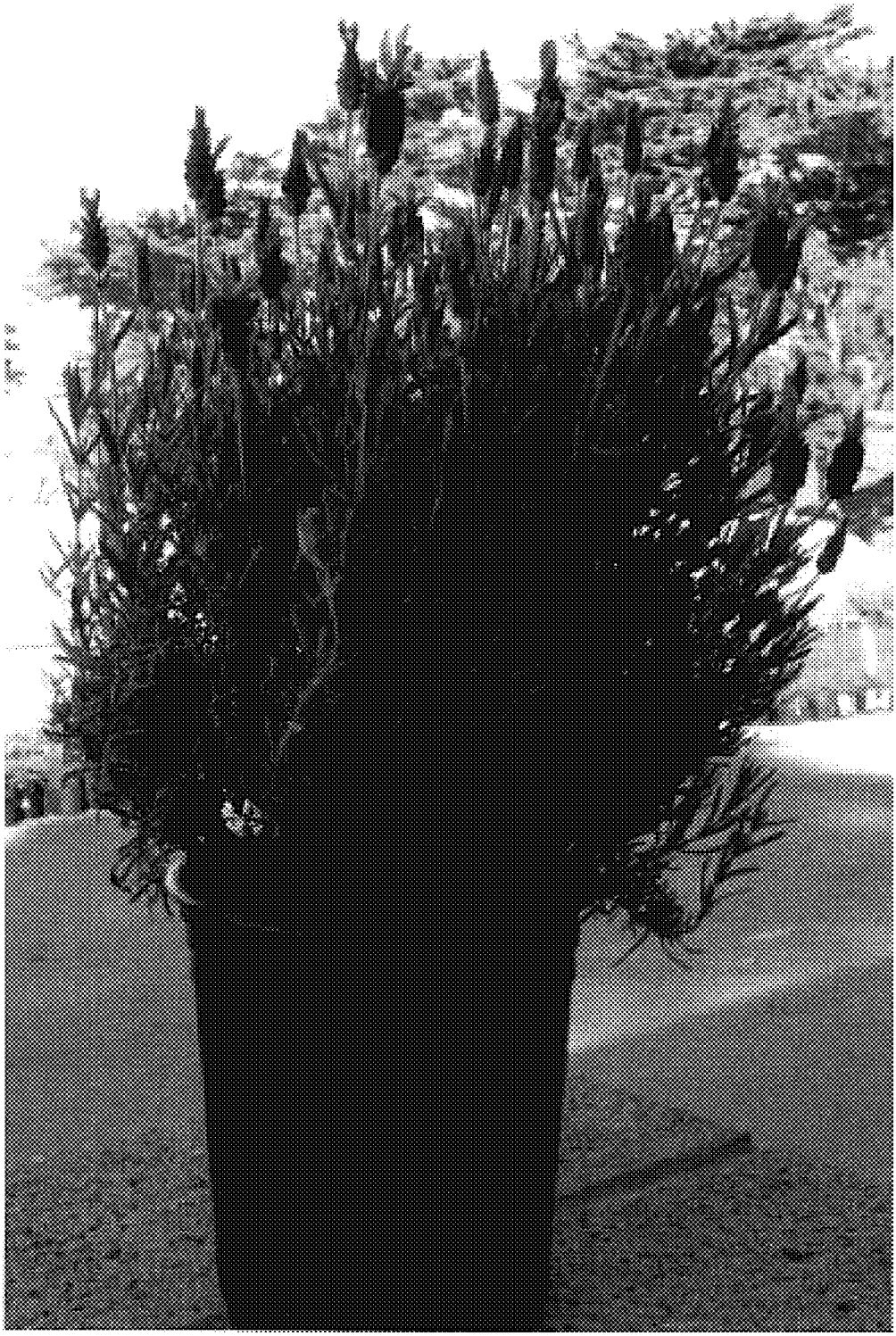

The following is a detailed description of the new cultivar as grown outdoors in one-gallon containers for six months under commercial nursery conditions in Folsom and Pescadero, Calif. The phenotype of the new cultivar may vary with variations in environmental, climatic, and cultural conditions, as it has not been tested under all possible environmental conditions. The color determination is in accordance with the R.H.S. Colour Chart of The Royal Horticultural Society, London, England, except where general color terms of ordinary dictionary significance are used.

General description:

*Botanical classification.*—*Lavendula stoechas* 'HanCev'.

*Parentage.*—Branch mutation of *Lavendula stoechas* 'Otto Quasti'.

*Blooming habit.*—Blooms from March to October in Pescadero, Calif. with heavier bloom in spring.

*Plant habit.*—Dense shrub-like columnar form, most pronounced in spring, with upright lateral branches.

*Height and spread.*—Reaches about 66 cm in height and 71 cm in spread in nice months.

*Weather tolerance.*—'HanCev' has shown very good tolerance to rain and wind, surviving temperatures ranging from 20° F. to over 100° F.

*Diseases and pests.*—More resistant to powdery mildew than is typical for *Lavandula stoechas* cultivars, no other susceptibility or resistance has been observed.

*Root description.*—Densely fibrous, freely branched.

Propagation and growth:

*Propagation.*—Terminal stem cuttings.

*Growth.*—Vigorous.

*Root initiation.*—About 25 days during spring and summer under greenhouse conditions at an average temperature of 75° F.

*Root development.*—Roots develop in 60 to 70 days at 75 to 80° F., during summer months under ambient light to fully develop a 2.5 inch rose pot.

Stem description:

*Stem shape.*—Square.

*Stem color.*—Young; 138B to 138C, mature wood; N199B with striations of N199C.

*Stem surface.*—Pubescent when young, becomes woody as it matures near base.

*Branching.*—Freely branched with lateral branches emerging near the base of the main stems rather than from axillary nodes, average of 40 lateral branches on a plant developed in a one-gallon container.

Foliage description:

*Leaves.*—Opposite arrangement, linear in shape, broadly cuneate base, sessile attachment, mucronate apex, entire margins, finely pubescent on upper surface and lower surface, average of 2.5 cm in length and 3 mm in width, strongly aromatic with mint-like fragrance, color: developing foliage upper and lower surface; 139C, mature foliage upper surface; 138B, mature foliage lower surface; N138C, internode length about 2 cm., venation is pinnate-reticulate with color matching leaf and conspicuous mid rib.

Inflorescence description:

*Inflorescence type.*—Small flowers arranged in compact terminal verticillasters with showy terminal sterile bracts.

*Inflorescence number.*—1 per lateral stem.

*Inflorescence fragrance.*—None detected.

*Lastingness of inflorescence.*—About 16 to 18 days with individual flowers lasting about 3 days, flowers not persistent, sterile bracts persistent.

*Inflorescence size.*—Average of 5 cm in depth and 2.5 cm in diameter; spike portion is about 2.5 cm in height and 1.2 cm in width, with sterile bracts portion at apex about 2.5 cm in height and 2.5 cm in width.

*Peduncles.*—Strong and erect, 5 to 8 cm in length and about 2 mm in diameter, surface is pubescent, color is 138B to 138C.

*Inflorescence bud.*—Average of 2.2 cm in height and 8 mm in width, ovate-oblong in shape, 138B and 138C in color with apex 83C to 83D in color.

*Fertile flowers.*—Tubular flowers arranged in compact cylindrical shaped verticillasters comprised of 6 to 9 rows, average of 60 flowers per verticillaster, fertile bracts; cordate in shape, about 8 mm in length and 7 mm in width, Venation 138A to 138B in color with N82C between veins, tomentose on upper and lower surface, entire margins, mucronate apex, cuneate base, flower size; about 8 mm in length and 4 mm in width, calyx; comprised of 5 sepals fused into oblong tube, about 5 mm in length and 1.5 mm in width, 138C in color, surface is tomentose, petals; five with base fused into tube, tube is about 3 mm in length and 1 mm in width, lobes are about 2 mm in length and width, roughly spatulate in shape, N89A in color on upper and lower surface, glabrous and velvety surface, rounded apex, margin primarily entire with some irregularly lobes.

*Sterile bracts.*—About 6 in a single whorl at apex of verticillaster, average of 2.5 cm in length and 7 mm in width, oblanceolate in shape, broadly acute apex, cuneate base, entire margins, surface is glabrous and iridescent, color of upper and lower surface is N82A with venation 83B (opening and mature), held primarily upright and curved inward with some twisting.

Reproductive organs:

*Pistils.*—1, stigma is reniform in shape, 1.5 mm in length and width, 84B in color with a tomentose surface, style is about 4 mm in length and 138D in color with a tomentose surface, ovary is very small and 138A in color.

*Stamens.*—4, anthers are oval in shape, about 1 mm in length, 83B in color, pollen is scarce and 16A in color.

*Fruit and seeds.*—No fruit or seed development has been observed under the trial conditions.

It is claimed:

1. A new and distinct cultivar of lavender plant named 'HanCev' as herein illustrated and described.

* * * * *